United States Patent [19]

Tan et al.

[11] Patent Number: 4,774,083

[45] Date of Patent: Sep. 27, 1988

[54] NOVEL PHARMACEUTICAL TABLETS

[75] Inventors: Hong S. Tan, Bleiswijk; Bernardus B. M. Wegman, Hoofddorp, both of Netherlands

[73] Assignee: Gist-Brocades N.V., Delft, Netherlands

[21] Appl. No.: 76,264

[22] Filed: Jul. 22, 1987

Related U.S. Application Data

[62] Division of Ser. No. 858,013, Apr. 30, 1986, Pat. No. 4,711,777.

[30] Foreign Application Priority Data

May 2, 1985 [EP] European Pat. Off. .......... 85-220692

[51] Int. Cl.$^4$ .................. A61K 9/20; A61K 31/74
[52] U.S. Cl. ..................................... 424/79; 424/465; 424/486; 424/501; 514/960

[58] Field of Search ................ 424/79, 465, 486, 501; 514/960

[56] References Cited

U.S. PATENT DOCUMENTS

| | | | |
|---|---|---|---|
| 3,091,574 | 5/1963 | Coletta et al. | 424/79 |
| 4,209,513 | 6/1980 | Torode et al. | 514/960 |
| 4,711,777 | 12/1987 | Tan et al. | 424/79 |

*Primary Examiner*—Shep K. Rose
*Attorney, Agent, or Firm*—Bierman & Muserlian

[57] ABSTRACT

Novel tablets comprising (a) 80 to 98% by weight of a mixture of trimethoprim and/or an acid addition salt thereof and a sulfonamide and/or a salt thereof in a weight ratio of 1:20 to 20:1 and (b) a pharmaceutically acceptable synthetic ion exchange resin having improved disintegration times and other properties and a process for their preparation.

3 Claims, No Drawings

NOVEL PHARMACEUTICAL TABLETS

PRIOR APPLICATION

This application is a division of copending U.S. patent application Ser. No. 858,013 filed Apr. 30, 1986, now U.S. Pat. No. 4,711,777.

STATE OF THE ART

Pharmaceutical tablets containing a mixture of 2,4-diamino-5-(3,4,5-trimethoxybenzyl)-pyrimidine (trimethoprim) and a sulfonamide are well known for the treatment of microbially-infected animals and humans and they usually contain trimethoprim and a sulfonamide in a ratio of 1:5 and the dosages of the mixture commonly given to adult patients are from 100 to 1000 mg. When conventional pharmaceutical techniques are used, the amount of active ingredients in a tablet should not exceed 80% by weight as a larger percentage will give tablets with poor physical properties such as a high disintegration or dissolution time, a high friability value or a low hardness value. Conventional tablets containing high doses of trimethoprim and a sulfonamide consequently have a large size which makes them difficult for a patient to swallow.

Attempts have been made to produce tablets with more than 80% of the said ingredients which still show satisfactory physical characteristics. Such a tablet is disclosed in British Pat. No. 1,499,672 wherein tablets containing trimethoprim and a sulfonamide such as sulfamethoxazole are prepared which contain 80 to 98% (w/w) of active ingredients. In addition to the active ingredients, the tablets contain a disintegrating agent having a swelling capacity greater than 5 ml/g and a granulating agent. The prescribed particle size, defined in terms of "weight median diameter", of the active ingredients is less than 40 μm, preferably much less. According to the patent, the tablets have a disintegration time of from 5 minutes and 25 seconds to nine minutes. In practice, when the disintegration agent is a strongly swelling agent, it becomes slimy and sticky on contact with a small quantity of liquid and this tends to commence already in the mouth and may result in a lingering bitter aftertaste.

OBJECTS OF THE INVENTION

It is an object of the invention to provide novel tablets containing at least 80% by weight of a mixture of trimethoprim and a sulfonamide and a process for their preparation.

It is another object of the invention to provide an improved method of combatting bacterial infections in warm-blooded animals.

These and other objects and advantages of the invention will become obvious from the following detailed description.

THE INVENTION

The tablets of the invention are comprised of (a) 80 to 98% by weight of a mixture of trimethoprim and/or an acid addition salt thereof and a sulfonamide and/or a salt thereof in a weight ratio of 1:20 to 20:1 and (b) a pharmaceutically acceptable synthetic ion exchange resin. The tablets do not have to contain large amounts of lactose or other hydrophilic agents such as corn starch and microcrystalline cellulose.

The use of ion exchangers in the preparation of solid pharmaceutical compositions is already known, e.g. from British Pat. No. 791,281, but this patent does not disclose a method for the preparation of compositions with a high percentage of active ingredients. The compositions described therein contain a relatively large amount of other excipients, particularly lactose, which by its hydrophilic character promotes the penetration of liquid into the tablet.

It will be appreciated that the ion exchange resin should be pharmaceutically acceptable and this implies that the ion exchange resin should not have a biological effect of its own in the doses used and that it should have a high degree of purity and a small particle size. Pharmaceutically acceptable ion exchange resins meeting these requirements are available, such as resins sold under the trade name Amberlite ®.

In view of the poor solubility of trimethoprim, it would be expected that tablets with an acceptable disintegration time could only be obtained by using a swelling agent with a high swelling capacity as described in British Pat. No. 1,499,672 but it has surprisingly been found that such a swelling agent is not necessary in the tablets of the invention. With the ion exchange resins of the invention, substantially shorter disintegration times were obtained and the ion exchange resins used in the tablets of the invention have the advantage that they do not give a slimy, sticky mass in contact with a liquid.

Preferred ion exchange resins are copolymers of divinylbenzene with styrene or methacrylic acid and phenol-polyamines, particularly the divinylbenzene copolymers. Most preferred are weakly acidic cation exchange resins consisting of methacrylic acid-divinylbenzene copolymers with free carboxyl groups such as Amberlite IRP-88. The ion exchange resin is preferably used in an amount from 1 to 8% by weight of the total tablet, more preferably 2 to 6%. The ratio of trimethoprim and sulfonamide is preferably 1:5 and a preferred sulfonamide is sulfamethoxazole (3-(4-aminobenzenesulfonamido)-5-methyl-isoxazole).

The tablets may also contain excipients commonly used in pharmacy such as fillers, binders, swelling agent, lubricating agents, wetting agents, granulating agents, flavoring agents and coloring agents. Examples of such additives are polyvinylpyrrolidone magnesium stearate, highly purified silicon dioxide, sodium dioctylsulfosuccinate, cellulose derivatives such as sodium carboxymethylcellulose and gelatin.

For the purpose of the invention, trimethoprim and the sulfonamide may be used as such or in the form of pharmaceutically acceptable salts, i.e. salts which are not harmful for the human or animal organism in the doses to be administered. Examples of such salts are acid addition salts such as hydrohalides (e.g. hydrochloride or hydrobromide), citrate, lactate, glutaminate and methylsulfonate of trimethoprim and the salts of sulfonamides with bases such as sodium hydroxide, ammona, and amines (e.g. alkanolamines such as ethanolamine).

The novel process of the invention for the preparation of the tablets comprises mixing trimethoprim and a sulfonamide, granulating the mixture with a suitable liquid, mixing the granulate with the other ingredients and compressing tablets from the mixture obtained. The granulating liquid is preferably a protic solvent such as ethanol or water or mixtures thereof which may contain one or more additives such as binding agents and wetting agents, for instance polyvinylpyrrolidone, sodium dioctylsulfosuccinate, gelatin or sorbitol. The preferred solvent is ethanol. The ion exchange resin may be mixed with the active agents to be incorporated in the granulate, or it may also be added entirely or partly after granulation. The tablets of the invention show satisfactory hardness and duriability and they comply with the usual standards with respect to disintegration time.

The invention also includes dispersable tablets and their preparation. Such tablets may be obtained by incorporating a relatively large amount of a disintegrating agent, preferably 4 to 6% by weight and suitable disintegrating agents for dispersable tablets are Amberlite resins of the types IRP 88, IRP 67M and IRP 69M.

In the following examples there are described several preferred embodiments to illustrate the invention. However, it should be understood that the invention is not intended to be limited thereto.

The tablets in the Examples were compressed on a Hoko excenter press and the hardness was measured with a Schleuniger 2E apparatus and the disintegration time was determined with an Erweka disintegration apparatus according to BP 80. In Examples 4,5 and 6 the disintegration was measured in water of 20° C. and in the other Examples in water of 37° C.

EXAMPLE 1

1200 g of sulfamethoxazole, 240 g of micronized trimethoprim and 28.8 of Amberlite IRP 88 were mixed for 15 minutes in a Turbula mixer. The mixture was granulated in a Hobart mixer with a solution of 28.8 g of PVP K30 in 350 ml of a water-ethanol mixture (1:1 v/v) and after 10 minutes, another 150 ml of the water-ethanol mixture were added. The moist mixture was ground in an Apex mill spread out on trays and dried overnight at 40° to 45° C. The granulate was sieved through a Frewitt apparatus with a 1.25 mm screen and the sieve granulate was mixed for two minutes in a Turbula mixer with 5 g of magnesium stearate and 5 g of Aerosil 200 V (highly purified silicon dioxide) per kg of granulate. The mixture obtained was pressed into tablets with a diameter of 11 mm, a hardness of 120N and a weight of 520 mg. Friability was 0.3% and disintegration time was 45 seconds. Also, oblong tablets were compressed with a hardness of 170N and a weight of 1020 mg. Friability of these was 0.4% and disintegration time was 45 seconds.

EXAMPLE 2

A mixture of 400 g of sulfamethoxazole and 80 g of micronized trimethoprim was granulated in an Erweka kneader with a solution of 9.6 g of PVP K30 in 160 ml of ethanol/water (1:1 v/v). The granulate obtained was dried at 50° C. and then sieved through a Frewitt apparatus with a 1.0 mm screen. The granulate was mixed with 9.6 g of Amberlite IRP 88 for 10 minutes on a rolling road and after addition of 2.5 g of magnesium stearate and 2.5 g of Aerosil 200 V, tablets were pressed with a diameter of 11 mm and a weight of 480 mg. Hardness was 100N and disintegration times was 30 seconds.

EXAMPLE 3

A mixture of 600 g of micronized sulfamethoxazole, 120 g of micronized trimethoprim and 14.4 g of Amberlite IRP 88 was granulated in a Topo-granulator (mini-Topo) with a solution of 14.4 g of PVP K30 in 275 ml of ethanol. The granulate was dried in the mini-Topo and sieved through a Frewitt apparatus with a 1.0 mm screen. A part of the granulate was mixed with 0.5% of Aerosil 200 V and 0.75% of magnesium stearate and then compressed into tablets with a diameter of 11 mm and a weight of 522 mg. Hardness was 110N and disintegration time was 30 seconds.

Another part of the granulate was sieved through a Frewitt apparatus with a 0.63 mm screen and 49 g of the sieved fraction were mixed with 1.5 g of Amberlite IRP 88, 0.75% of magnesium stearate and 0.50% of Aerosil 200 V. The mixture was compressed into tablets with a diameter of 13 mm and a weight of 860 mg. Hardness was 70N and disintegration time was 20 seconds.

EXAMPLE 4

80 g of micronized sulfamethoxazole, 16 g of micronized trimethoprim and 5.0 g of Amberlite IRP 88 were mixed in a Hobart mixer. After 5 minutes, a granulating liquid consisting of 2.0 g of PVP K30, 0.04 g of Aerosol OT (sodium dioctylsulfosuccinate) and 40 ml of ethanol was added with stirring to obtain a granulate which was dried in a fluid bed drier and pressed through a 0.80 mm screen. The granules were mixed with 0.5 g of Aerosil 200 V and 0.75 g of magnesium stearate and tablets were compressed with a diameter of 13 mm and a weight of 730 mg. Hardness was 140N and disintegration time was less than 1 minute.

EXAMPLE 5

The procedure of Example 4 was repeated using 1.0 g of PVP K30 and the tablets had a hardness of 150N, a weight of 660 mg and a disintegration time of less than 1 minute.

EXAMPLE 6

80.0 g of micronized sulfamethoxazole, 16.0 g of micronized trimethoprim, 5.0 g of Amberlite IRP 88 and 5.0 g of Elcema G 250 (a cellulose derivate) were mixed in a Hobart mixer and granulated with a solution of 1.0 g of PVP K30 in 50 ml of ethanol. The granulate was dried on a fluidized bed and pressed through a 0.80 mm screen. The granulate was mixed for two minutes with 0.75 g of magnesium stearate and 0.50 g of Aerosil 200 V and tablets were compressed with a diameter of 13 mm and a weight of 678 mg. Hardness was 140N and disintegration time was less than 1 minute.

EXAMPLE 7

60 mg of micronized sulfamethoxazole, 12 g of micronized trimethoprim and 1.4 g of Amberlite IRP 88 were mixed in a Hobart mixer for 5 minutes and the mixture was granulated with a solution of 1.55 g of gelatin in 30 ml of ethanol/water (1:1 v/v). The granulate was dried at 60° C. and pressed through a 1.0 mm screen. The granules were mixed for two minutes with 0.75% of magnesium stearate and 0.5% of Aerosil 200 V in a Turbula mixer and convex tablets were pressed with a diameter of 11 mm and a weight of 523 mg. Hardness was 130N and disintegration time was 25 seconds.

EXAMPLE 8

The procedure of Example 7 was repeated with 1.5 g of sorbitol instead of gelatin and the tablets had a weight of 550 mg, a hardness of 170N and a disintegration time of 60 seconds.

EXAMPLE 9

60 g of micronized sulfamethoxazole and 12 g of micronized trimethoprim were mixed for 5 minutes in a Hobart mixer and the mixture was granulated with a solution of 1.5 g of gelatin in 30 ml of ethanol/water (1:1 v/v). The granulate was dried at 60° C. and pressed through a 1.0 mm screen. The granules were mixed for 10 minutes with 1.4 g of Amberlite IRP 88 and subsequently for 2 minutes with 0.75% magnesium stearate and 0.5% Aerosil 200 V. Tablets were compressed with a diameter of 11 mm and a weight of 525 mg. Hardness was 140N and distingegration time was 35 seconds.

EXAMPLE 10

The procedure of Example 9 was repeated with 1.5 g of sorbitol instead of gelatin and the tablets had a weight of 540 mg and a hardness of 170N and disintegrated in 90 seconds.

EXAMPLE 11

60 g of micronized sulfmethoxazole, 12 g of trimethoprim and 1.4 g of Amberlite IRP 88 were stirred in a Hobart planetary mixer for 5 minutes and the mixture was granulated with 32 ml of ethanol/water (1:1 v/v). The granulate was dried at 60° C. and pressed through a 1.0 mm screen. The granulate was mixed for two minutes with 0.75% of magnesium stearate and 0.5% of Aerosil 200 V in a Turbula mixer and convex tablets were pressed with a diameter of 11 mm and a weight of 540 mg. Hardness was 160N and disintegration time was 15 seconds.

EXAMPLE 12

60 g of micronized sulfmethoxazole and 12 g of micronized trimethoprim were mixed in a Hobart planetary mixer for five minutes and the mixture was granulated with 30 ml of ethanol/water (1:1 v/v). The granulate was dried at 60° C. and it was then comminuted in a Frewitt apparatus with a 1.0 mm screen. The granules were mixed for 10 minutes on a rolling road with 1.4 g of Amberlite IRP 88 and then 0.75% magnesium stearate and 0.5% Aerosil 200 V were added, after which mixing was continued for two minutes. The mixture was compressed into convex tablets with a diameter of 11 mm and a weight of 535 mg. Hardness was 150N and disintegration time was 15 seconds.

EXAMPLE 13

A mixture of 80 g of micronized sulfmethoxazole, 16 g of micronized trimethoprim and 4.8 g of Amberlite IRP 88 was granulated with a solution of 50 mg of Aerosol OT in 45 ml of ethanol and the moist mass was press through a 2.0 mm screen and was then dried in a vacuum oven at 60° C. The dried granulate was sieved through a 0.8 mm scrcen and mixed with a 0.75% magnesium stearate and 0.5% Aerosil 200 V and tablets were pressed with a diameter of 15 mm and a weight of 1000 mg. Hardness was 160N and disintegration time was 15 seconds.

EXAMPLE 14

I Preparation of granulate 400 g of micronized sulfamethoxazole and 80 g of micronized trimethoprim were mixed in an Erweka kneader and subsequently granulated with a solution of 9.6 g of polyvinylpyrrolidone K30 and 0.6 g of Aerosol OT in 150 ml of alcohol. The granulate was dried at 60° C. and sieved in a Frewitt apparatus with a 1.0 mm screen.

II Preparation of tablets a. 40 g of the granulate were mixed for 10 minutes with 1.6 g of Amberlite IRP 64M (weakly acidic ion exchange resin in the H$^+$ form) and then 0.200 g of Aerosil 200 V and 0.300 g of magnesium stearate were added. Mixing was continued for 2 minutes and tablets were pressed with a diameter of 13 mm and a weight of 710 mg. Hardness was 160N and disintegration time was 6 minutes.

b. The procedure described under a was repeated with Amberlite IRP 67M (strongly basic ion exchange resin in the Cl$^-$ form) instead of Amberlite IRP 64M. The tablets had a weight of 705 mg, a hardness of 130N and a disintegration time of less than one minute.

c. The procedure described under a was repeated with Amberlite IRP 69M (strongly acidic ion exchange resin in the Na$^+$ form) instead of Amberlite IRP 64M. The tablets had a weight of 715 mg, a hardness of 130N and a disintegration time of less than one minute.

d. The procedure described under a was repeated with Amberlite IRP 88 instead of Amberlite IRP 64M and the tablets had a weight of 675 mg, a hardness of 200N and a disintegration time of less than one minute.

EXAMPLE 15

20 g of sulfadiazine and 4 g of trimethoprim were mixed and the mixture was granulated with 12 ml of a solution of 1% (w/v) polyvinylpyrrolidone in water/ethanol (1:1). The granulate was dried at 60° C. and it was then pressed through a 1.0 mm screen. The granules were successively mixed with 2% Amberlite IRP-88, 0.5% Aerosil 200 V and 0.5% magnesium stearate and the mixture was compressed into convex tablets with a diameter of 11 mm and a weight of 530 mg. The hardness was 120N and the disintegration time less than 60 seconds.

EXAMPLE 16

A mixture of 30 g of sulfamethoxazole and 2 g of trimethoprim was granulated with a solution of 0.64 g of polyvinylpyrrolidone in 12 ml of ethanol/water (1:1) and the granulate was dried at 60° C. It was then pressed through a 1.0 mm screen and further mixed successively with 2% Amberlite IRP-88, 0.5% Aerosil 200 V and 0.5% magnesium stearate. Convex tablets were compressed with a diameter of 11 mm and a weight of 600 mg. The hardness was 200N and the disintegration time less than 30 seconds.

EXAMPLE 17

The procedure of Example 16 was repeated with 30 g of trimethroprim instead of 2 g and 2 g of sulfamethoxazole instead of 30 g. The convenx tablets had a diameter of 11 mm, a weight of 538 g, a hardness of 60N and a disintegration time less than 15 seconds.

EXAMPLE 18

Tabless containing 98% active ingredients and 1.35% ion exchange resin were prepared as follows: 204.2 g of micronized sulfamethoxazole, 40.8 g of micronized trimethoprim and 3.4 g of Amberlite IRP 88 were mixed in a Hobart mixer and granulated with a solution of 125 mg of sodium dioctylsulfosuccinate in 75 ml of 96% ethanol. The granulate was dried on a plate at 60° C. and passed through a 0.8 mm screen. 750 mg of sieved (0.5 mm) Aerosil 200 V were added and mixed for 10 minutes in a Turbula mixer. 750 mg of sieved (0.5 mm)

magnesium stearate were added and mixed for another 5 minutes. The resulting mixture was compressed into round tablets with a diameter of 13 mm and a weight of 612 mg. Hardness was 150N and disintegration time was 35 seconds.

EXAMPLE 19

Tablets containing 80% active ingredients and 4.5% ion exchange resin were prepared as follows:

a. 133.3 g of micronized sulfamethoxazole, 26.7 g of micronized trimethoprim and 9 g of Amberlite IRP 88 were mixed in a Hobart mixer and granulated with a solution of 100 mg of sodium dioctysuccinate in 50 ml of 96% ethanol. The moist granulate was pressed through a 2 mm screen and dried on a plate at 60° C. The dried granulate was sieved through a 0.8 mm screen and mixed for 10 minutes in a Turbula mixer with 28.7 g of Avicel pH 102 and 1 g of screened (0.5 mm) Aerosil 200 V. 1.2 g of magnesium stearate were then added and mixed for another 5 minutes. The mixture was compressed into round tablets with a 13 mm diameter and a weight of 750 mg. Hardness was 170N and disintegration time was 25 seconds.

b. The procedure of Example 19a was repeated with 9 g of Amberlite IRP 276 (strongly basic ion exchange resin in a $Cl^-$ form). The round tablets with a diameter of 13 mm and a weight of 750 mg had a hardness of 160N and a disintegration time of 15 seconds.

Various modifications of the tablets and methods of the invention may be made without departing from the spirit or scope thereof and it is to be understood that the invention is intended to be limited only as defined in the appended claims.

What we claim is:

1. A process for the preparation of rapidly disintegrating tablets comprising forming a mixture of 80% to 98% by weight of trimethoprim or a salt thereof and a sulfonamide or a salt thereof, in a weight ratio of 1:20 to 20:1 granulating the mixture with a suitable liquid, mixing the granulate with one or more other excipient ingredients and compressing tablets from the mixture and adding 1 to 8% by weight of an ion exchange resin as the essential disintegrant during the preparation of the granulate or to the granulate.

2. The process of claim 1 wherein the liquid used in the granulation is a protic solvent.

3. The process of claim 2 wherein the protic solvent is ethanol.

* * * * *